United States Patent [19]

Nakagawa et al.

[11] Patent Number: 5,142,647
[45] Date of Patent: Aug. 25, 1992

[54] MAGNUS MEASURING APPARATUS

[75] Inventors: Osamu Nakagawa; Nobuo Hosoya; Noriaki Kuno; Takao Hirose, all of Hiratsuka, Japan

[73] Assignee: Japan Tobacco, Inc., Tokyo, Japan

[21] Appl. No.: 509,849

[22] Filed: Apr. 17, 1990

[30] Foreign Application Priority Data

Apr. 18, 1989 [JP] Japan .................................. 1-96270
Apr. 18, 1989 [JP] Japan .................................. 1-96271

[51] Int. Cl.⁵ .......................................... G06F 15/20
[52] U.S. Cl. ............................... 364/508; 364/413.01; 364/413.02
[58] Field of Search ............... 364/508, 413.01, 413.02; 73/800, 803, 805, 834

[56] References Cited

U.S. PATENT DOCUMENTS 4,031,746  6/1977  Furuta et al. ...................... 364/508

Primary Examiner—Parshotam S. Lall
Assistant Examiner—Ellis B. Ramirez
Attorney, Agent, or Firm—Armstrong, Nikaido, Marmelstein, Kubovcik & Murray

[57] ABSTRACT

An improved magnus measuring apparatus for providing an automatic initial setting at high speed in testing a plurality of biological specimens which moves elastically with beats, wherein a tensile force is applied on a specimen by moving the transducer connected thereto with use of a motor to be driven and stopped under the control of a control unit, and thereby the rotating speed of the motor is increased gradually at least for a predetermined period of time from the start and then kept at high speed for bringing a bottom value of the tensile force to enter an extent of preliminarily set initial value. In another aspect of the invention, a detected tensile force is sampled for detecting a peak of the tensile force and a threshold value is renewed in succession from the initial setting based on detected peak and bottom values, and then detecting a peak of the tensile force being caused from the beats of the specimen, hence said tensioning is so controlled as to adjust the detected bottom value to be in an extent of preset tensile force.

3 Claims, 9 Drawing Sheets

MAGNUS MEASURING APPARATUS

BACKGROUND OF THE INVENTION

1. Field of the Invention

This invention relates to a magnus measuring apparatus and, more particularly, to a magnus measuring apparatus for use in a magnus method for primary screening of pharmaceutically active substances.

2. Description of the Prior Art

The magnus method is a measuring method for measuring effects of pharmaceutical solutions against a biological specimen such as a skeleton muscle, a nerve muscle, an atrium or smooth muscle and the like being capable of performing an elastic movement, wherein said biological specimen is immersed in a nutritious solution by maintaining a tension being applied thereto and thereby reacted with various pharmaceutical solutions as keeping the function of the specimen.

The effect on the specimen by the pharmaceutical solution is, for instance, evaluated by measuring an amount of elongation of the specimen through a change of tension or a change of length thereof. Accordingly, there has been used in the prior art is a magnus measuring apparatus which can afford to measure an amount of elongation as well as a beat rate of the specimen by way of transferring a change of tension of the specimen into an electric signal.

In the prior art magnus measuring apparatus, a receptacle called a magnus tube for containing a nutritious solution as well as a pharmaceutical solution is employed, the specimen is provided with strings at both ends thereof, and thereby the lower end of the string is hooked on a projection formed in the magnus tube whilst the upper end of the string is secured to a transducer. The transducer is then moved up and down against the magnus tube for applying a tensile force to the specimen. In measuring, a periodic change of tension based on the elastic movement of the specimen is recorded by a pen recorder or an equivalent in accordance with an electric signal derived from the transducer which moves correspondingly with the tensile force applied on the specimen.

In case of employing a transducer which converts a tension to an electric signal, it is required to keep an initial tension to be applied on the specimen constant at the time when the specimen is immersed in a nutritious solution. That is, in such type of measuring method, whenever a type of a pharmaceutical solution is changed, the solution in the tube is replaced with another solution and thereby the specimen is required to be washed before immersing, and thus the initial tension of the specimen to be immersed in a new nutritious solution should always be set to a constant value.

Heretofore, in order to retain the constant initial tension for the specimen, for instance, if the transducer is mounted on a stud with use of a mounting screw, there required are repetitive operations of tightening or loosening of the mounting screw in adjusting a vertical position of the transducer by confirming the tension being applied to the specimen with reference to, for an example, a chart recorded by a pen-recorder in accordance with a converted electric signal which is derived from the transducer in response to the tension of the specimen.

In accordance with the prior art magnus measuring apparatus, a measured value of the tension applied on the specimen have to be read from the recorded chart with use of calipers and the like, this results in a time-consumption and, as it has been described above, the setting operation for the constant initial tensioning of the specimen has been a problem. Especially, in case of performing various tests simultaneously by using a plurality of specimens, there caused are a considerable time-comsumption and an inconvenience in operation.

Further, there is a need of automating the initial setting operation, however, in the initial setting, it is necessary to set the tension of the specimen to a bottom value of the tensile force varying in a periodic manner, thus the beats of the specimen as well as the bottom value thereof should be detected automatically in advance of automating the initial setting.

It is therefore an object of this invention to solve such problems encountered in the prior art and to provide a magnus measuring apparatus wherein the initial setting operation is automated.

It is another object of this invention to provide a magnus measuring apparatus wherein the initial setting operation is automated in such a manner as to vary a driving mode of a motor from a low to high speed operation in response to a control signal derived from a control unit in order to achieve a high speed automation.

It is still another object of this invention to provide a magnus measuring apparatus wherein a threshold value being set preliminarily in the initial setting can be renewed based on a detected tensile force being applied on a specimen.

It is a further object of this invention to provide a magnus measuring apparatus wherein a peak of the tensile force causing from beats of a specimen is detected after renewing a threshold value being set preliminarily.

It is still further object of this invention to provide a magnus measuring apparatus wherein a bottom value of the tensile force that varies periodically is so adjusted as to be within a preliminarily set extent of the tensile force simultaneously with detecting a peak of the tensile force causing from beats of a specimen after renewing a threshold value being set preliminarily.

SUMMARY OF THE INVENTION

The subject invention provides a magnus measuring apparatus comprising a transducer for detecting a tensile force being applied on a specimen by pulling the specimen at one end thereof whilst the other end of which is fastened, tensioning means for applying a tensile force on a specimen by moving the transducer against the specimen in response to an amount of rotations of a motor, and a control unit for adjusting the tensile force to be applied on the specimen by controlling the tensioning means, being characterized in that, there included is motor control means for controlling the driving and stops of the motor of the tensioning means in both directions based on a control signal form the control unit and for controlling a motor speed in such a manner as to increase the rotating speed gradually at least for a predetermined period of time from the start of thereof, wherein the control unit controls the switching of the rotary direction of the motor through the motor control means in order to adjust the detected tensile force by the transducer to be a value within an extent of tensioning being set preliminarily.

In another aspect of the invention, the control unit performs sampling of the tensile force detected by the transducer with a certain interval, wherein a peak of the tensile force is detected based on a threshold value renewed in succession from the initial setting and the sampled tensile force attained through the sampling, a peak value and a bottom value of the tensile force are detected in turn based on a tensile force sampled after the foregoing peak detection for a renewal of the threshold value correspondingly to the detected peak and bottom values, and then a peak of the tensile force being caused from the beats of the specimen is detected.

In still another aspect of the invention, the control unit performs sampling of the tensile force detected by the transducer with a certain interval, wherein a peak of the tensile force is detected based on a threshold value renewed in succession from the initial setting and the sampled tensile force attained through the sampling, a peak value and a bottom value of the tensile force are detected in turn based on a tensile force sampled after the foregoing peak detection for a renewal of the threshold value correspondingly to the detected peak and bottom values, a peak of the tensile force being caused from the beats of the specimen is then detected, and thereby controlling the tensioning means to adjust the detected bottom value to be in an extent of preset tensile force.

DESCRIPTION OF THE PREFERRED EMBODIMENTS

Figure 6:
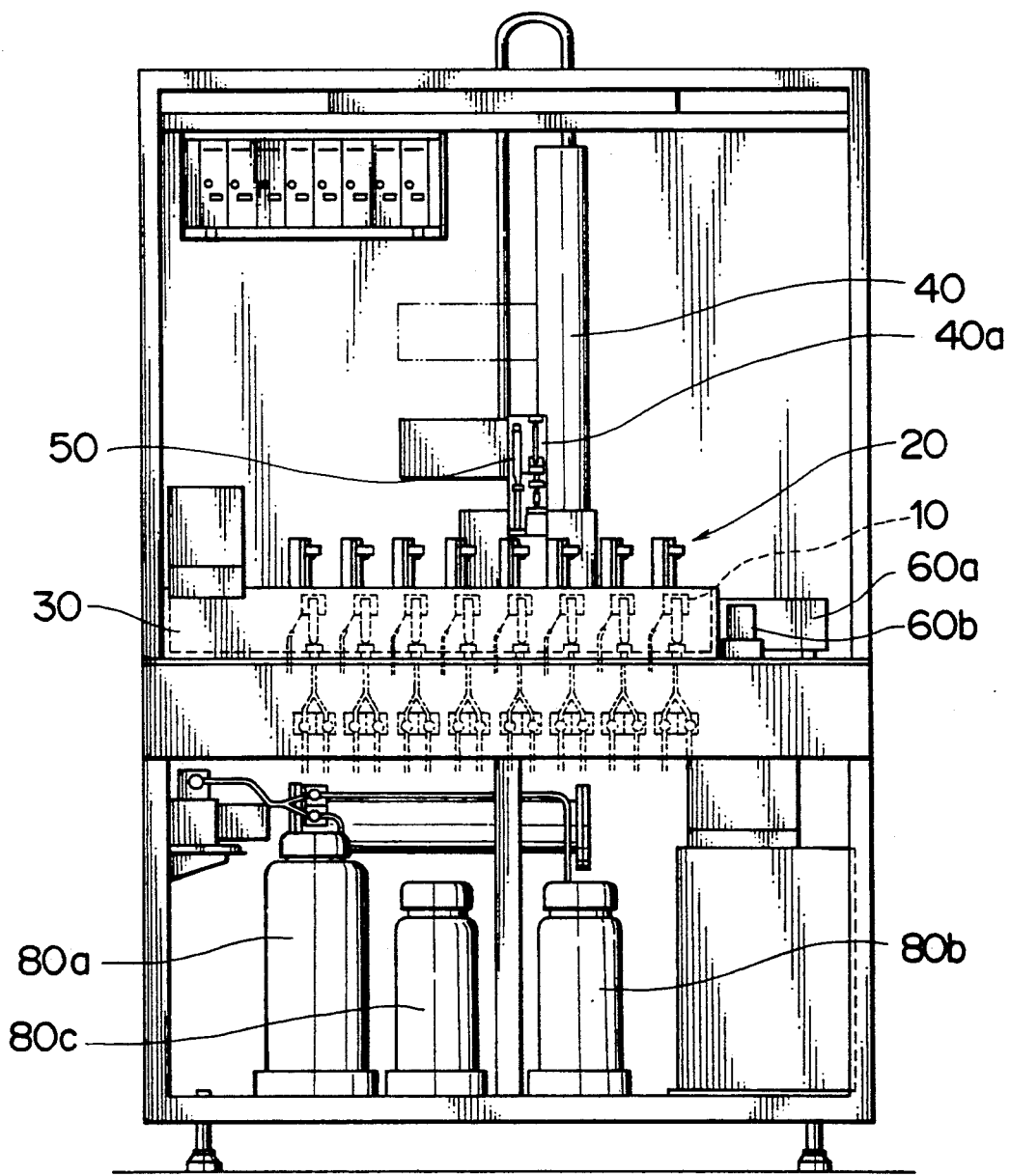
FIG. 6 is a front view of a magnus measuring apparatus embodying the principles of this invention.
Figure 7:
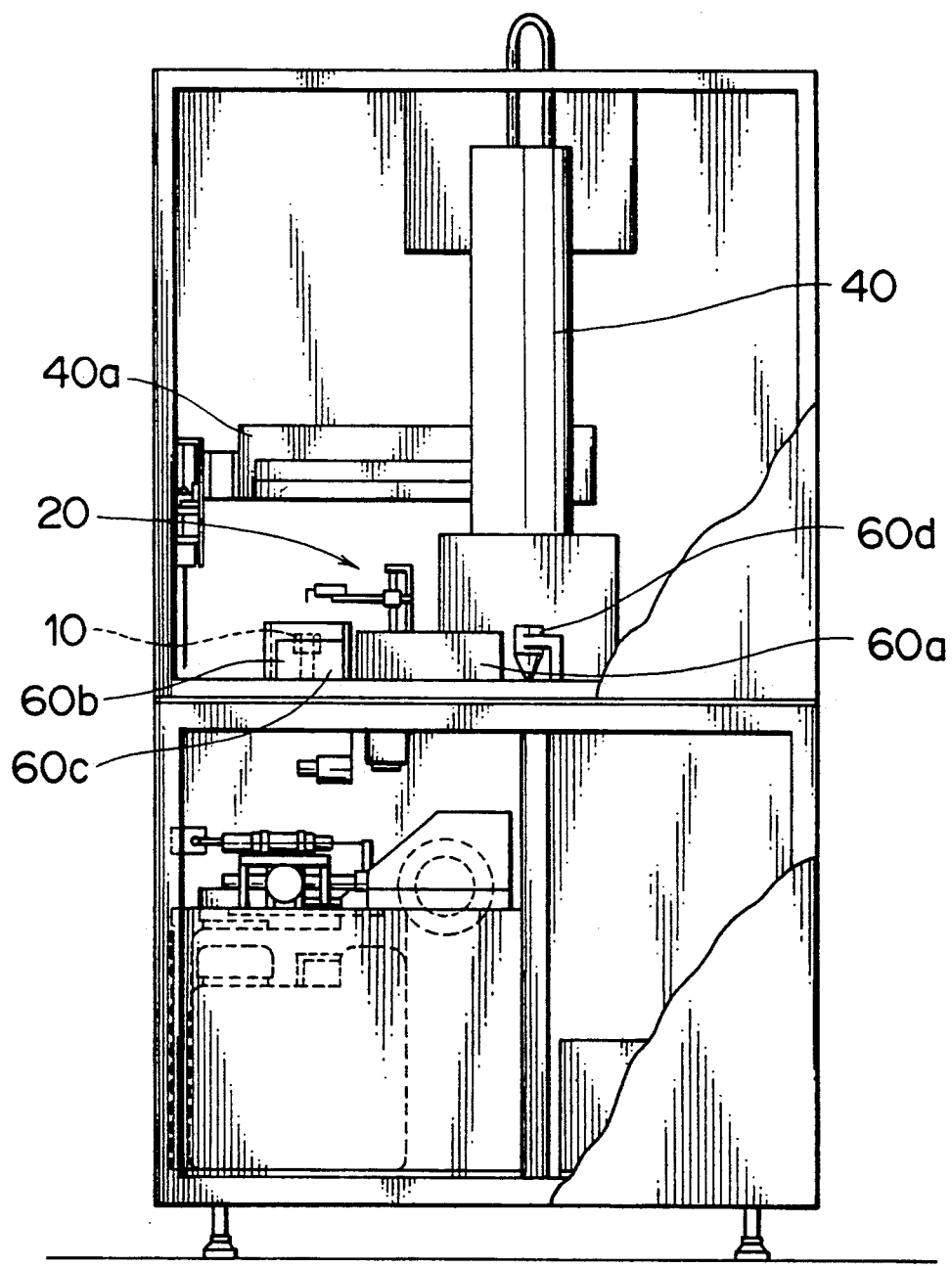
FIG. 7 is a side view partly in cross section of the magnus measuring apparatus embodying the principles of this invention.

Referring now to the drawings, and particularly to FIG. 6 and FIG. 7, there are shown a front view and a side view of a magnus measuring apparatus embodying the principles of this invention.

In the respective drawings, numeral 10 denotes a magnus tube prepared for immersing a specimen into a nutritious solution, numeral 20 denotes a transducer for detection a tensile force of the specimen as an electric signal, and thereby the magnus tubes 10, eight in total, are placed in a thermostat and the same number of transducers 20 are installed for pairing with each of the magnus tubes 10. Further, in the same FIG's, numeral 40 denotes a transfer robot of the type having a cylindrical coordinates in movements and this transfer robot 40 is furnished with a syringe 50 at an arm 40a thereof for injecting a pharmaceutical solution into the magnus tubes and, within an extent of moving area of the arm 40a, there provided are a cooling thermostat 60 for containing bottles, which are for pharmaceutical solutions, and washing vessels 60b, 60c, which are for washing the syringe 50, as well as a rhote type washing vessel 60d besides the magnus tubes 10.

In accordance with the magnus measuring apparatus of the embodiment of this invention, a number of specimens and a plurality of pharmaceutical solutions can be examined and measured with use of the eight magnus tubes 10 and, further, the injection of the pharmaceutical solutions into the magnus tubes and the washing of the syringe 50 are performed automatically by transferring the syringe 50 through the operation of the transfer robot 40.

Figure 8:
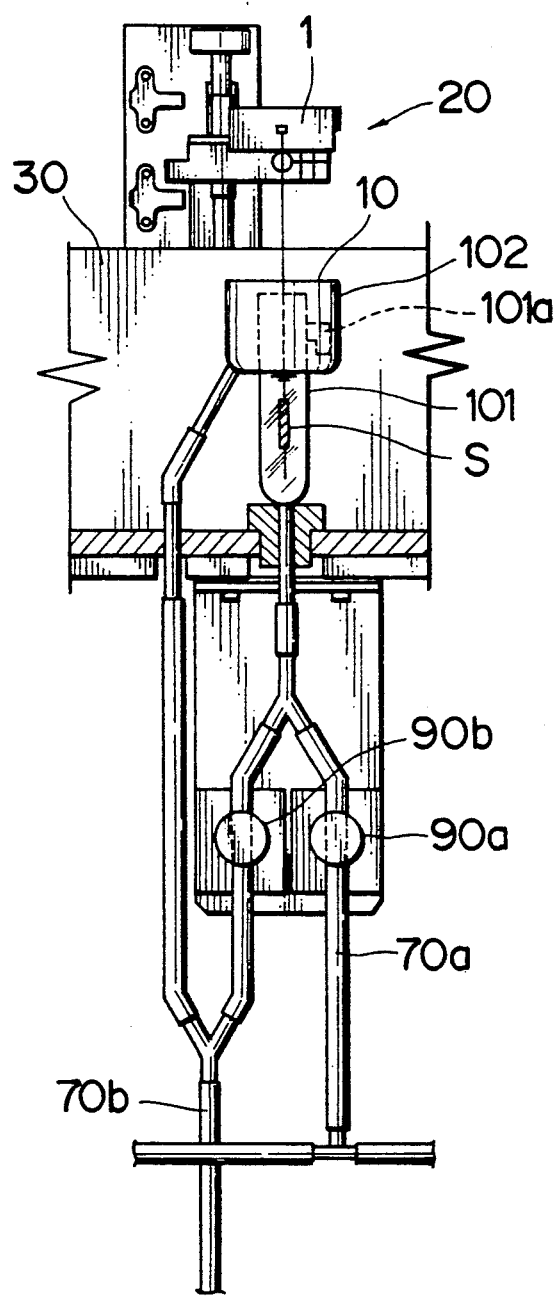
FIG. 8 is a front view of the magnus tube herein used in the embodiment of this invention.

Each of the magnus tubes 10 is made up of an elongated tube member 101 having an overflow passage 101a at the upper part thereof, which is shown more specifically in FIG. 8, and an outer tube member which surrounds the upper part of the elongated tube member 101. The bottom portion of the elongated tube member 101 is connected to an inlet passage 70a for a nutritious solution and an outlet passage 70b through a connecting Y-piece as well as gum pipes and all that the bottom portion of the outer tube member 102 is connected to the outlet passage 70b in a similar manner.

At the lower part of the apparatus, there contained are a nutritious solution tank 80a for storing the nutritious solution, a wash liquid tank 80b for storing a wash liquid and a waste liquid tank 80c for collecting the waste liquid, whereby the pouring or draining of the nutritious solution is carried out by controlling the switching of a solenoid valve 90a installed in the inlet passage 70a and a solenoid valve 90b installed in the outlet passage 70b.

Figure 4A:
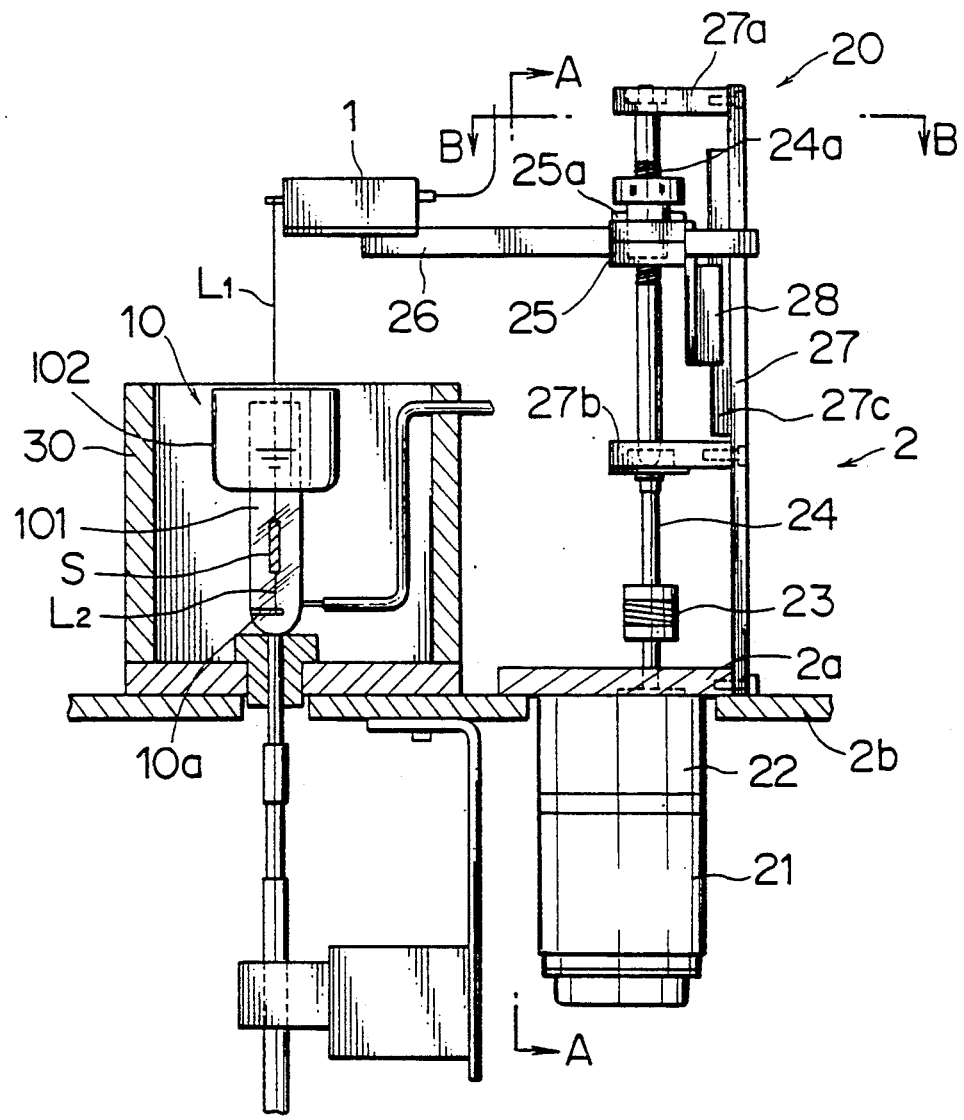
FIG. 4a, 4b and 4c are side, front and top views of a transducer herein installed in the embodiment of this invention.
Figure 4C:
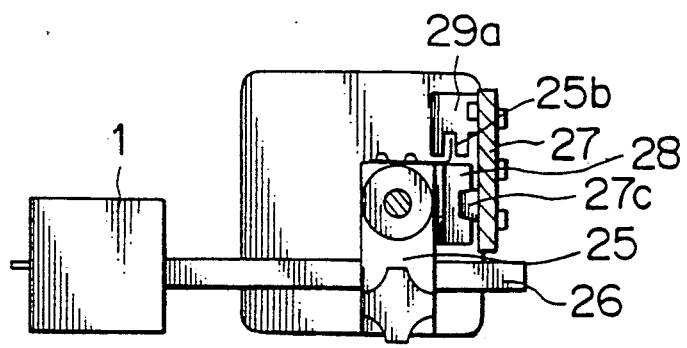
Figure 4B:
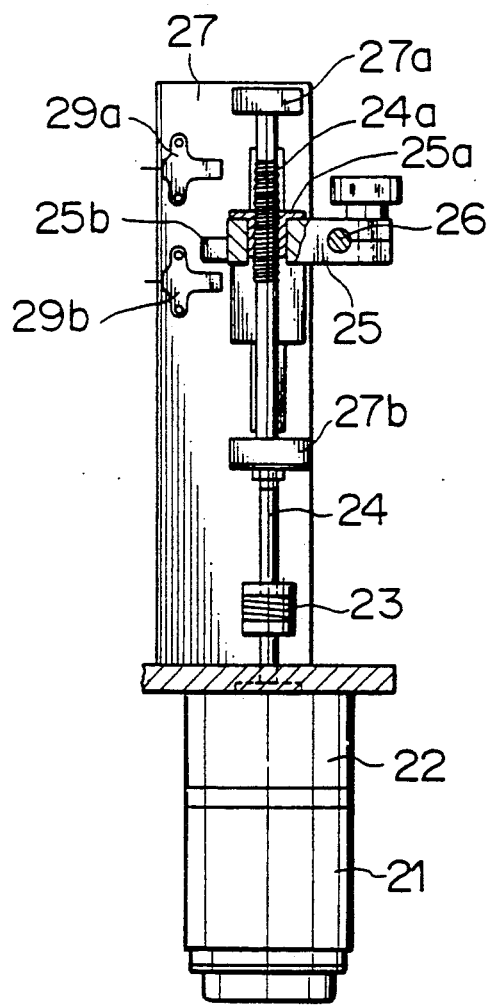

Now referring to FIG. 4, there is shown the transducer 20 employed in the embodiment of this invention, wherein FIG. 4a is a side view, FIG. 4b is a partial view from line A—A of FIG. 4a, and FIG. 4c is a partial view from line B—B of FIG. 4a.

A specimen S is provided with a string L1 at the upper end and a string L2 at the lower end, and thereby the string L2 at the lower end side is hooked on a projection 10a within the magnus tube whilst the string L1 at the upper end side is hung from a transducer unit 1 and the specimen is immersed into the nutritious solution contained in the magnus tube 10.

The transducer 20 includes the transducer unit 1 which transforms a tensile force applied on the specimen into an electric signal and elevator means 2 which ascends or descends the transducer unit 1 for tensioning. The electric signal from the tranducer unit 1 is fed to a control unit which will be described more specifically in the following. In addition, a strain gage or a transducing member employing a differential inductance may be utilized as the transducer unit 1.

The elevator means 2 comprises an AC motor 21 to be driven under the control of the control unit which will be described later, a reduction gear 22 connected directly to the AC motor 21, a thread shaft 24 coupled to a drive shaft of the reduction gear 22 through a coupling unit 23, and a mounting unit 25 for mounting a support arm 26 carrying the transducer unit 1 at the one end thereof. The reduction gear 22 is secured to a table 2b by utilizing a plate 2a. Further, a mounting base 27 studding from the plate 2a carries bearings 27a, 27b, whereas the thread shaft 24 is supported by these bearings 27a, 27b.

The thread shaft 24 has a feed screw 24a at one portion thereof and a nut 25a secured to the support arm mounting unit 25 is engaged with the feed screw 24a. The support arm mounting unit 25 has a guide 28 to be moved up and down along a rail 27c provided on the mounting base 27 and, therefore, the support arm mounting unit 25 can be moved up and down without any rotation around the vertical axis.

Accordingly, when the thread shaft 24 is rotated through the drive of the AC motor 21, the support arm mounting unit 25 is moved up and down for changing a height of the transducer unit 1 depending on a rotary direction of the AC motor 21 and, then, changing a tensile force to be applied on the specimen in response to the height of the transducer unit 1. At an upper portion of the mounting base 27, there provided are an upper limit proximity switch 29a and a lower limit proximity switch 29b respectively for detecting a metal member 25b attached to one side of the support arm mounting unit 25. Thus, the upper limit position and the lower limit position of the support arm mounting unit 25 is detected by these proximity switches 29a, 29b and each detected signal is fed to the control unit.

The thread shaft 24 is provided with the feed screw 24a within the limits of required amount for moving up and down the transducer unit 1 whilst the remaining portions thereabove and therebelow are formed smaller in diameter, therefore, the support arm mounting unit 25 is released from its engagement with the feed screw 24a at the upper and lower parts thereof. With this arrangement, the elevator means 2 itself is prevented effectively from damage to be caused by the driving force of te AC motor 21 even if the AC motor 21 is rotated continuously because of, for instance, a failure of the upper limit proximity switch 29a or lower limit proximity switch 29b beyond the limits.

Figure 1:
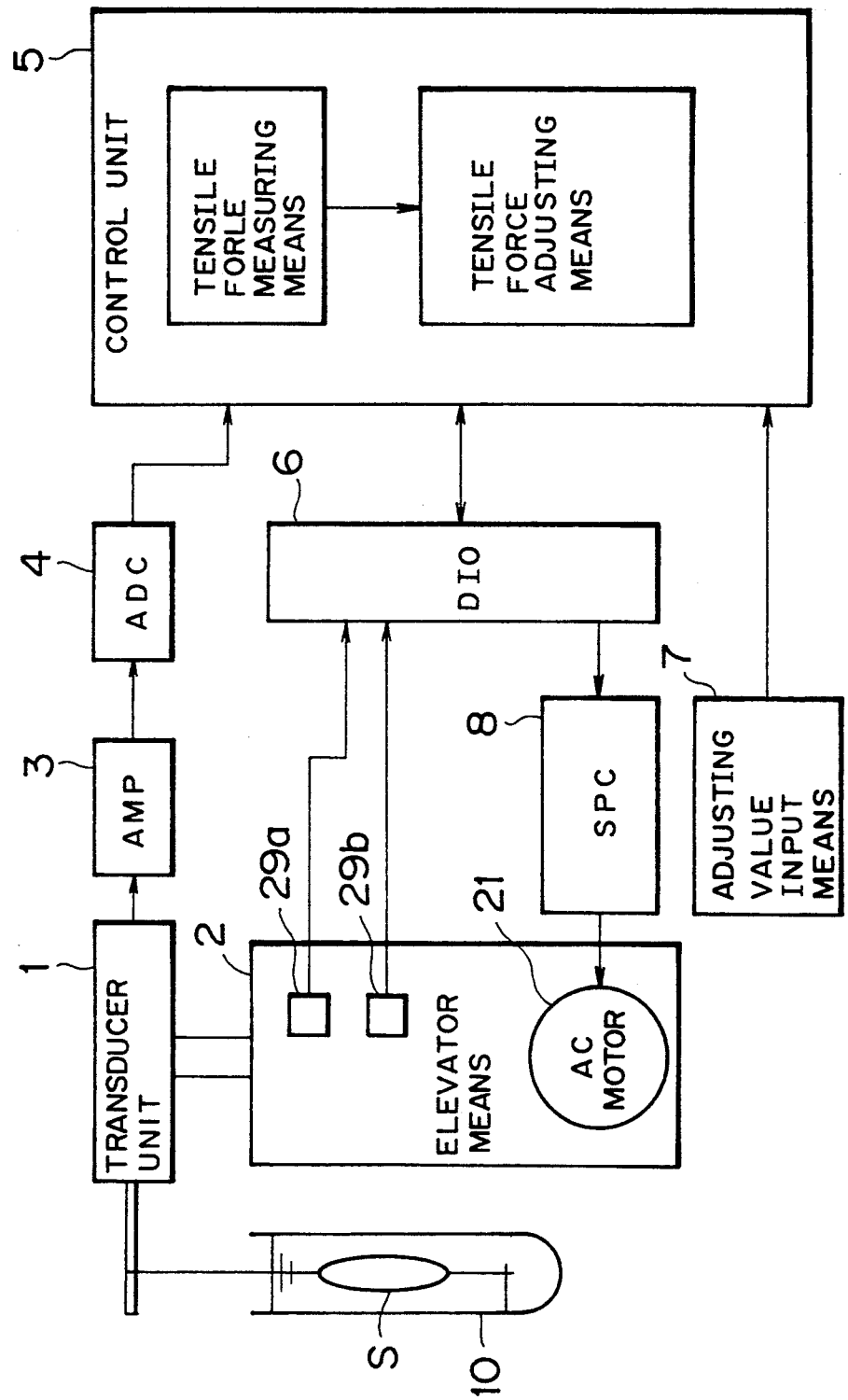
FIG. 1 is a block diagram showing an embodiment of this invention.

FIG. 1 is a block diagram showing a control system of the embodiment of this invention, wherein an electric signal derived from the transducer unit 1 is fed to the control unit 5 through an amplifier 3 and an A/D convertor (ADC) 4 and detected signals from the upper limit proximity switch 29a and the lower limit proximity switch 29b are also fed to the control unit 5 through a digital I/O port (DIO) 6. Further, the upper and lower limiting values for the tensile force being selected to have a predetermined extent as a target tension value in the initial setting are fed from an adjusting value input means 7.

A speed controller (SPC) 8 controls the AC motor 21 to drive in either rotary direction or to stop the rotation thereof in accordance with a control signal form the control unit 5, and thereby controls a rotating speed of the AC motor 21 to increase gradually for a predetermined period of time from the start of driving and maintain a constant rotating speed upon reaching a required rotating speed. A "speed controlled motor" equipped with a slow start function, for instance, made by Oriental Motor Co., Ltd., may be used for the AC motor 21 and the speed controller 8 therefor.

The control unit 5 is made up of a microcomputer and the like and includes a tensile force measuring means and a tensile force adjusting means to be implemented by control flowcharts hereinafter described more specifically. The tensile force measuring means measures a tensile force to the specimen S based on data which is fed through the ADC 4 whilst the tensile force adjusting means performs the initial setting automatically by controlling the speed controller 8 in such a way as to bring a measured tensile force into the limits or extent of tensile force (a preset tensile force) being preliminarily set by the adjusting value input means 7.

In addition to the above, the tensile force measuring means samples the data being fed through the ADC 4, whereby detects a peak of tensile force in the beats of the specimen S and also measures a tensile force at the state of relaxation (a bottom value) preceding to the peak detection. Further, the tensile force adjusting means performs the initial setting automatically by controlling the speed controller 8 in such a way as to bring a measured bottom value into the limits or extent of tensile force being preliminarily set by the adjusting value input means 7.

The control unit 5 stores the state of the transducer such as every state of ascending, descending and stopping of the transducer unit 1. The control unit 5 also stores a flag (hereinafter called "excess flag") indicating a state that a measured tensile force exceeds the upper limit of the preset tensile force and a flag (hereinafter called "extent flag") indicating a state that a measured tensile force is within the limits of the preset tensile force. The control unit 5 further stores such state of the transducer unit 1 that whether it has reached the upper end position or the lower end position based on the signal from either the upper limit proximity switch 29a or the lower limit proximity switch 29b. Hence, the control for the transducer is performed in accordance with these stored contents and a measured tensile force.

The specimen such as the atrium muscle makes elastic movement periodically, it is therefore needed for such specimen to adjust the initial setting against the state of relaxation of the elastic movement. For this type of adjustment, the control unit 5 detects a peak of the periodically varying tensile force at each transducer and performs the initial adjustment based on the tensile force at the state of relaxation (the bottom value) preceding to the peak detection above.

In accordance with the embodiment of this invention as described above, there provided are a plurality of pairs (8 pairs) of transducers and magnus tubes, the control unit stores the state of each transducer, eight transducres in total, in its inner memory and performs the peak detection and the control of initial setting in time sharing for each transducer. Further, there provided is a peak detection counter (PEAK) for counting a number of states of no peak detection in succession, whereas the adjustment is judged to end in failure if the count reaches to a predetermined numbers as it is described more particularly hereinafter.

Figure 2:
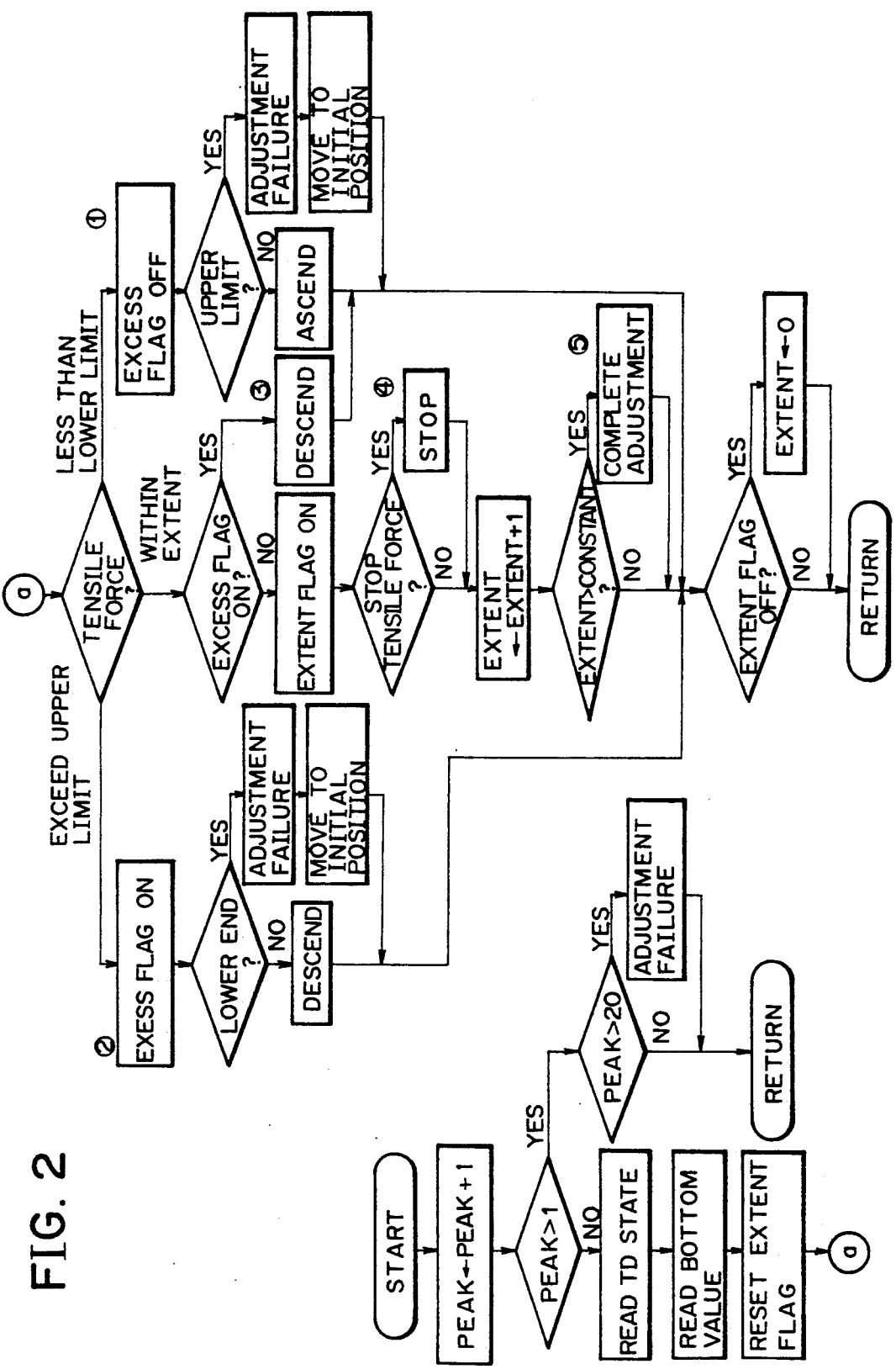
FIG. 2 is a flowchart showing the operation steps for initial tensile force setting performed by the embodiment of this invention.
Figure 3A:
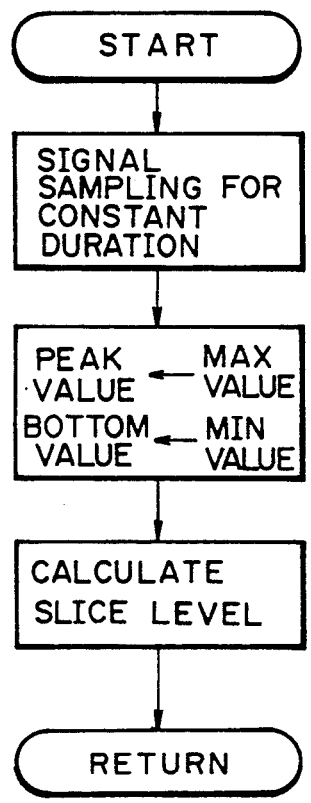
FIG. 3a and 3b are flowcharts showing the operation steps for initial value setting and peak detection performed by the embodiment of this invention.
Figure 3B:
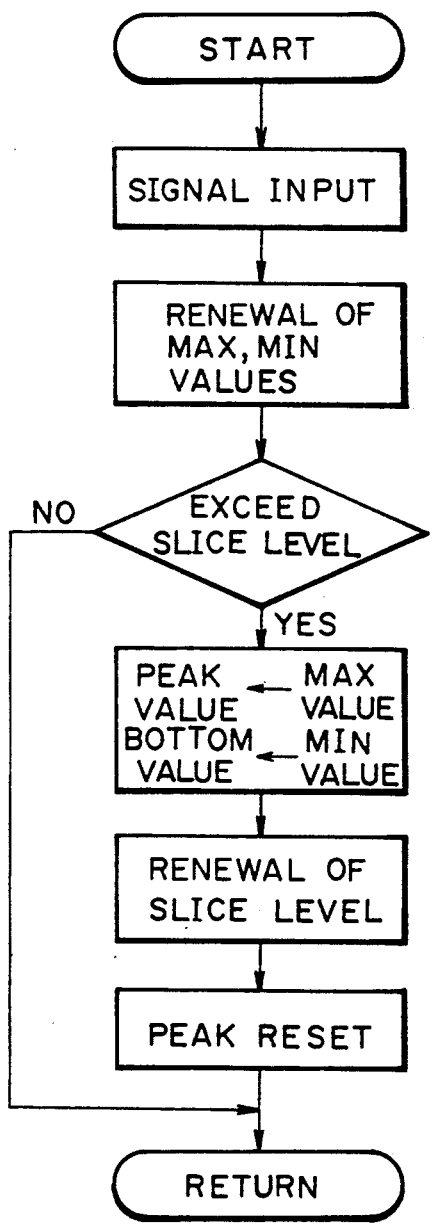

FIG. 2 and FIG. 3 together form flowcharts showing the operational steps performed by the control unit 5, more specifically, the flowcharts show subroutines to be initiated by a main routine which controls each of 8 transducers in time sharing, wherein FIG. 2 is the flowchart showing the operational steps in the initial tensile force setting, FIG. 3a is the flowchart showing the operational steps in setting initial values for peak, bottom and threshold values, and FIG. 3b is the flowchart showing the operational steps in the peak detection.

The peak detection flow shown in FIG. 3b is activated with a period of 5 ms for each transducer whilst the initial tensile force setting flow shown in FIG. 2 is activated with a period of 1 sec for each transducer. The activation of the peak detection flow with the period of 5 ms may be implemented by adopting a timer interruption system and the like and a signal derived from the transducer unit is sampled with every 5 ms interval.

The operational steps for one transducer will now be described more specifically. As it is shown in FIG. 3a, the control unit 5 samples the tensile force with a predetermined period (for instance, 5 ms period) for a predetermined period of time (for instance, 5 sec), and thereby assigning the maximum value of the sampled values to an initial peak value and that the minimum value of the sampled values to an initial bottom value, hence an initial threshold value (for instance, a slice level in close to the peak value) against these peak and bottom values is determined in the next place.

Upon initiation of the peak detection flow with the period of 5 ms (FIG. 3b), the maximum value is renewed if a tensile force exceeds the preceding maximum value and that the minimum value is renewed if a tensile force is less than the preceding minimum value at the time when a signal representing an applied tensile force is received. The peak detection flow is then returned to the main routine if the tensile force is less than the threshold value for performing the peak detection of another transducer in a time sharing manner. However, if the tensile force exceeds the threshold value, the maximum value at that time is assigned to a new peak value and that the minimum value to a new bottom value, hence the threshold value is renewed accordingly based on the renewed peak and bottom values, and the peak detection counter (PEAK) corresponding to the measuring transducer is in turn reset to "0".

In like way, a peak value as well as a bottom value are stored in the memory at the time when a peak for each transducer is detected and all that the detection of the peak is also stored by the state of resetting of the peak detection counter (PEAK).

Aforesaid excess flag and extent flag have already been reset, therefore, the peak detection counter (PEAK) counts up by 1 if the initial tensile force setting flow shown in FIG. 2 is activated at every 1 sec, whereby it is decided in such a way as there is a "no peak detection" if the count of the peak detection counter is larger than 1, whilst it is decided that there is a "peak detection" if the count is at or less than 1 (that means 1). That is, since the peak detection counter is brought to a rest condition at every time when a peak is detected and increased in counting by 1 at every time when the initial tensile force setting flow is activated, the peak detection counter denotes 1 if there is the peak detection in the aforesaid decision process whilst denotes 1 over than the accumulated counts of successive states of no peak detection if there is the no peak detection in the decision process.

If no peak value is detected in the judging process, it is decided in turn whether or not the count of the peak detection counter is at or above a predetermined value ("20" in this embodiment), and the adjustment is decided to end in failure if the count exceeds the predetemined value, however, the program is returned to the main flow if the count is less than the predetermined value.

When there is a peak detection, the state of the transducer (TD) is read from the memory, and at the same time, reading off a measured tensile force (bottom value) at the time when the peak is detected and resetting the extent flag, hence there performed are following controls depending on a value of measured tensile force.

When the measured value exceeds the upper limit

It is decided whether or not the transducer is at its lower end by turning the excess flag "ON". If the transducer is at the lower end, the adjustment is decided to end failure and the transducer unit 1 is returned to its initial position where is preliminarily set, whereas if it is not at the lower end, the transducer is brought to a descending condition. After the decision has been made, the program is returned to the main flow if the extent flag is not "OFF", whereas if the extent flag is "OFF", the program is returned to the main flow after resetting a counter (hereinafter called an extent counter (EXTENT)) to "0", which counter is for indicating such a number of counts that the measured tensile force is within the extent.

When the Measured Value is Less Than the Lower Limit

It is decided whether or not the transducer is at its upper end by turning the excess flag "OFF". If the transducer is at the upper end, the adjustment is decided to end failure and the transducer unit 1 is returned to its initial position where is preliminarily set, whereas if it is not at the upper end, the transducer is brought to an ascending condition. After the decision has been made, the program is returned to the main flow if the extent flag is not "OFF", whereas if the extent flag is "OFF", the program is returned to the main flow after resetting the extent counter (EXTENT)) to "0".

When the Measured Value is Within the Limits

Firstly, the state of the excess flag is evaluated. If the excess flag is "ON", the transducer is brought to a descending condition whereas, the program is returned to the main flow if the extent flag is not "OFF" whilst the program is returned to the main flow after resetting the extent counter (EXTENT)) to "0" if the extent flag is not "OFF". If the excess flag is not "ON", it is decided whether or not the measured tensile force has reached a stop tensile force value which will be described later, if it has not, the extent counter (EXTENT) is increased in counting by 1, whereas if it has, the extent counter (EXTENT) is increased in counting by 1 after stopping the movement of the transducer.

Secondly, it is decided whether or not the counting of the extent counter (EXTENT) has exceeded a predetermined value being set preliminarily, and thereby a flag which indicates the completion of the adjustment is set only when the counting has reached the predetermined value. After the decision has been made, the program is returned to the main flow if the extend flag is not "OFF" whilst the program is returned to the main flow after resetting the extent counter if the extent flag is "OFF".

The aforesaid stop tensile force value is a tensile force value having a certain extent within the extent of preliminarily setting for applying tensile force, whereby the extent of the stop tensile force is determined by assigning the upper limit value of the preliminarily set tensile force to an upper limit and that an approximately 10%, for instance, larger value than the lower limit value of the preliminarily set tensile force to a lower limit. A vibration in the state of controlling, which is caused from the variation of the measuring tensile force, is evadible by providing some width between the lower limit value of the stop tensile force value and the lower limit value of the preliminarily set tensile force whereat the transducer is reversed its movement into ascendance.

Figure 5:
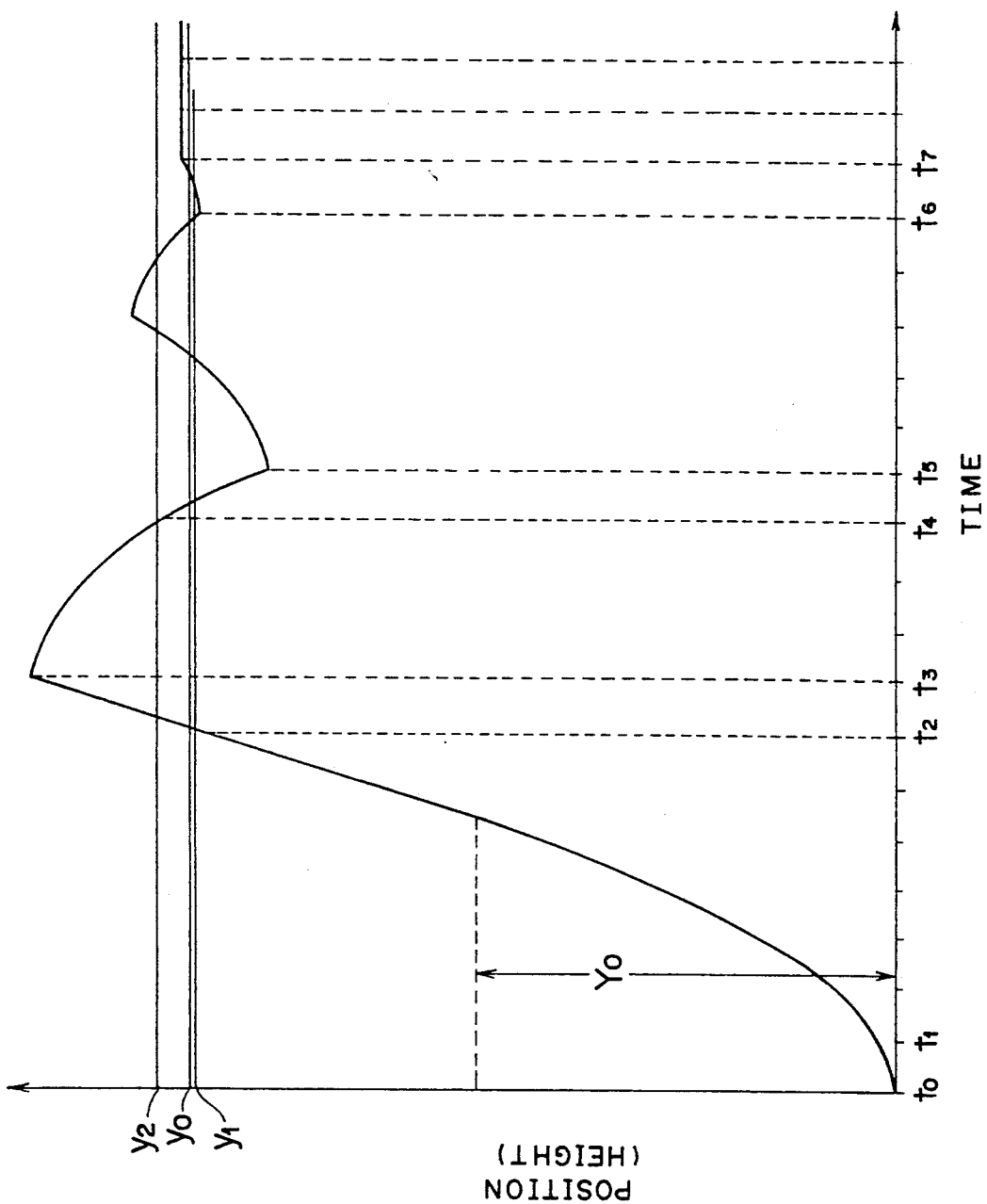
FIG. 5 is a timing diagram showing a change of state at the transducer under the control in the embodiment of this invention.

Referring now to FIG. 5, there is shown a schematic diagram illustrating a change of the state of the transducer in accordance with the control flows which have been described above. In FIG. 5, the axis of ordinates represents a position of the transducer unit 1 in the vertical direction, the axis of abscissas represents an elapsed time and a solid line represents a path of the transducer unit 1. Further, the character Yo denotes an imaginary displacement that correponds to an accelerating state of an AC motor 21 and the characters y0, y1, y2 denote positions that correspond respectively to the lower limit value of the stop tensile force value, as well as the lower limit value and the upper limit value of the preliminarily set tensile force.

An example of initial setting operation will be described in the following with reference to FIG. 5. It should be noted that operations identified with numbers (1)–(5) in the following description correspond to steps having the same numbers in the flowchart of FIG. 2.

As seen, at the initiation time of t0 of the control, a measured tensile force is less than the lower limit value y1, the transducer unit 1 is elevated for increasing a tensile force to a specimen and in turn the excess flag is turned "OFF"(1), and thereby the AC motor 21 is increased in rotating speed gradually for speeding up the elevation of the transducer unit 1 for high speed operation as the measured tensile force is less than the lower limit value y1 in a duration of the times t1–t2.

Upon exceeding the upper limit value y2 at time t3, the excess flag is turned "ON", the tranducer unit 1 is reversed its movement for descending (2) and is kept descending until the measured tensile force becomes less than the lower limit value at the time t5, whereby even if a measured tensile force becomes a value within the limits at the time t4 in a way of the descending, the state of the descending is maintained (3) since the excess flage is still at the state of turned "ON".

Since the measured tensile force becomes less than the lower limit at the time t5, the transducer unit 1 is again reversed its movement for ascending and the excess flag is turned "OFF" (1), thus the like process is repeated until the time t6.

When the transducer unit 1 is reversed for ascending at the time t6 and the measured tensile force becomes a value within the extent of the stop tensile force value (y0–y2) at the time t7, the movement of the transducer unit 1 is stopped becasue of the fact that the excess flag has already turned "OFF" at the time t6 (1) and thereby the extent counter (EXTENT) is increased in counting by 1 (4). Thereafter, the extent counter (EXTENT) is increased in counting at every time when the measured tensile force is brought into the extent of preliminary set tensile force in succession and the adjustment will complete when the count reaches to a predetermined value (5).

As it is apparent from the embodiment shown in FIG. 5, since the transducer unit 1 is moved at high speed within a high speed region by the AC motor 21 from the start of the control until the measuring tensile force approaches to its preliminarily set tensile force extent, it is possible to bring the transducer unit 1 at high speed to the target position where is corresponding to the preset tensile force extent, however, after the measuring tensile force has reached to the proximity of the preset tensile force extent, the reversing of the rotation of the AC motor may occur in a quick succession for providing the up and down movement of the tranducer unit, whereas the AC motor is driven in a low speed region immediately after the start of driving, thus there provided is an operation suited for a precise adjustment in the vicinity of the target position.

As it has been described above, in accordance with this invention, a bottom value which varies in response to the up and down movement of the transducer unit 1 is detected in succession after detecting a periodic peak of the tensile force caused by the beats of the specimen, an initial tensile force is adjusted based on the detected bottom value, and thus the initial tensile force setting can be performed automatically even for the specimen carrying beats.

Further, aforesaid peak detection is also carried out in a measurement after the completion of the initial setting, whereas the peak and bottom values at the time of peak detection as well as a period of peaks are stored in the memory for performing an automatic measurement of the beat rates of the specimen. The period of peaks can, for instance, be detected by utilizing a counter which counts a number of sampling between the successive peak detections.

It should be appreciated from the foregoing description that the present invention provides an improved magnus apparatus, wherein a tensile force is applied on a specimen by moving the transducer unit which detects the tensile force being applied on the specimen, a motor for driving the transducer unit is so controlled as to increase its rotating speed gradually for at least a predetermined period of time after the start of the motor, the tensile force detected at the transducer unit is brought into the extent of tensile force being preliminarily set by controlling a change of rotary directions of the motor, and thus the transducer unit is moved at high speed until the measured tensile force approaches to the present extent of tensile force whilst the transducer unit is moved at low speed when the measured tensile force is in the proximity of the preset extent of tensile force for providing a fast and accurate automatic initial setting. Further, a time required for the initial tensile force setting, especially, in an apparatus for measuring a number of specimens at the same time is considerably decreased and the usability of such apparatus is greatly improved.

Furthermore, in accordance with this invention, there is no need of employing expensive parts, such as a pulse generator and the like, nor a software for controlling the pulse generator as compared with the case employing a stepping motor or an equivalent, this results in the use of the simplified control software and the considerable decrease in the vibration.

As it has been described above, in accordance with a magnus measuring apparatus embodying the present invention, a peak value of the tensile force in detected based on a threshold value being revised in succession from the initial set value by sampling the tensile force of the specimen, and thereby the threshold value is revised based on the bottom and peak values at every time when the peak value detection is performed, the specimen beat rates can be measured automatically. Further, since the tensile force applying means is controlled in order to bring the detected bottom value into the extent of tensile force being preliminarily set at the time of initial setting, the initial setting can be performed automatically and the usability is greatly improved.

Although the present invention has been described with reference to the presently-preferred embodiments, it should be understood by those of ordinary skilled in the art that various modifications can be made without departing from the spirit and scope of the invention.

Accordingly, the invention is not to be limited except as by the appended claims.

What is claimed is:

1. In a measuring apparatus for measuring physical parameters of a specimen being subjected to one or more substances, including a transducer unit for detecting a tensile force being applied on a specimen by pulling the specimen at one end thereof whilst the other end of which is fastened, tensioning means for applying a tensile force on the specimen by moving the transducer against the specimen in response to an amount of rotations of a motor, and a control unit for adjusting the tensile force to be applied on the specimen by controlling the tensioning means, said measuring apparatus comprising:

specimen holding means, for storing the specimen during testing;

motor control means for controlling the driving and stopping of the motor of the tensioning means in both rotary directions based on a control signal from the control unit and for controlling a motor speed in such a manner as to increase the rotating speed gradually at least for a predetermined period of time from the start thereof; and fluid supply means, for supplying a fluid to said specimen holding means, wherein said control unit controls the switching of the rotary direction of the motor through the motor control means in order to adjust the detected tensile force by the transducer unit to be a value within an extent of tensioning being set preliminarily.

2. In a measuring apparatus for measuring physical parameters of a specimen being subjected to one or more substances, including a transducer unit for detecting a tensile force applied on a specimen, a control unit for measuring the tensile force based on a detected signal at the transducer unit, specimen holding means, for storing the specimen during testing, and fluid supply means for supplying a fluid to said specimen holding means, wherein said control unit performs sampling of the tensile force detected by the transducer unit with a certain interval, thereby a peak of the tensile force is detected based on a threshold value renewed in succession from the initial setting and the sampled tensile force attained through the sampling, a peak value and a bottom value of the tensile force are detected based on a tensile force sampled in a peak detection after said peak detection while the threshold value is renewed based on the detected peak and bottom values, and then a peak of tensile force being caused from the beats of the specimen is detected.

3. In a measuring apparatus for measuring physical parameters of a specimen being subjected to one or more substances, including a transducer for detecting a tensile force being applied on a specimen, tensioning means for applying a tensile force on the specimen, and a control unit for measuring the tensile force based on a detected signal at the tranducer and for adjusting the tensile force to be applied on the specimen by controlling the tensioning means based on the measured tensile force, specimen holding means, for storing the specimen during testing, and fluid supply means for supplying a fluid to said specimen holding means, wherein said control unit performs sampling of the tensile force detected by the transducer with a certain interval, thereby a peak of the tensile force is detected based on a threshold value renewed in succession from the initial setting and the sampled tensile force attained through the sampling, a peak value and a bottom value of the tensile force are detected based on a tensile force sample in a peak detection after said peak detection while the threshold value is renewed based on the detected peak and bottom values, a peak of the tensile force being caused from the beats of the specimen is detected, and then said tensioning means is so controlled as to adjust the detected bottom value to be in an extent of preset tensile force.

* * * * *